United States Patent [19]

Edwards et al.

[11] Patent Number: 5,163,228
[45] Date of Patent: Nov. 17, 1992

[54] GONIOMETER

[75] Inventors: Glenn R. Edwards; Frank Koenig, both of Palo Alto, Calif.

[73] Assignee: Greenleaf Medical Systems, Inc., Palo Alto, Calif.

[21] Appl. No.: 581,481

[22] Filed: Sep. 12, 1990

[51] Int. Cl.$^5$ .................................... G01B 3/56
[52] U.S. Cl. ................. 33/1 N; 33/1 PT; 33/512; 33/465
[58] Field of Search ............ 33/1 N, 1 PT, 511, 512, 33/471, 465, 504, 534, 784; 128/774, 782

[56] References Cited

U.S. PATENT DOCUMENTS

| | | | |
|---|---|---|---|
| 3,270,420 | 9/1966 | Simril | 33/471 |
| 4,442,606 | 4/1984 | Graham et al. | 33/1 PT X |
| 4,468,860 | 9/1984 | Rodengen | 33/784 |
| 4,771,548 | 9/1988 | Donnery | 33/471 X |
| 4,922,925 | 5/1990 | Crandall et al. | |
| 4,986,280 | 1/1991 | Marcus et al. | 33/512 X |

FOREIGN PATENT DOCUMENTS

| | | | |
|---|---|---|---|
| 0115620 | 8/1984 | European Pat. Off. | 128/782 |
| 2741978 | 3/1979 | Fed. Rep. of Germany | 33/471 |

Primary Examiner—Harry N. Haroian
Attorney, Agent, or Firm—Kirkpatrick & Lockhart

[57] ABSTRACT

A system for measuring an inputting range of motion data to a computer comprises a goniometer for measuring range of motion and for producing a range of motion signal from those measurements. A plurality of switches are carried by the goniometer for producing control signals. An interface device receives the range of motion signal and digitizes that signal to produce range of motion data. The interface device also receives the control signals which are used to control the input of the range of motion data to the computer.

8 Claims, 5 Drawing Sheets

Range of Motion - Fingers

Patient Name:

Date:

- ● Electrogoniometer
- ○ Manual

● Active  ○ Passive

○ Lateral & Rotational

Hand: ○ L  ● R

Note

Extension: 10, 15, 0, 0 / 0, 20, 0, 0 / 0, 20, 0, 0

Flexion: 0, 95, 87, 100 / 92, 110, 108, 95 / 45, 96, 93, 90

Hyperextension
● Positive (+)   ○ Negative (−)

measurements are:

92°

Next Exam
Calibrate
Clear Angle
Clear All
Help
Exam List

GONIOMETER

BACKGROUND OF THE INVENTION

1. Field of the Invention

The present invention is directed generally to instruments for conducting range of motion evaluations and, more specifically, to instruments for conducting range of motion evaluations of joints.

2. Description of the Background

Evaluation of the hands and the larger upper extremities, as currently performed in clinics and hospitals, consists of measurements of strength, range of motion, nerve sensation and graphic depiction of deformities of the hand, arm and shoulder. These measurements are required for pre-operative, post-operative, and periodic assessment of functional abnormality. To meet the requirements of most health and workman's compensation insurance, these measurements are standardized and reported in a consistent format throughout the United States. Evaluation techniques in other countries are quite similar, with expected changes in measurement units and reporting format.

Sufficient range-of-motion of any joint is critical for functionality. Because of the importance of range-of-motion, every joint has at least one measurement, and several have more than one measurement such as the wrist and shoulder. Measurements are typically compared between an injured and non-injured joint. These measurements can also be used to calculate an impairment rating for the particular joint or joints being evaluated. The impairment rating consists of a mathematical formula for calculating the usefulness of the joint or extremity being evaluated, given as a percent of being fully functional. The standard formula for calculating impairment ratings is set forth in the 1989 American Medical Association *Guides to the Evaluation of Permanent Impairment*.

In general, the goniometer is used to measure range-of-motion of the joints. In the present state of the art, goniometers generally consist of two (2) thin, flat members or halves of rigid or semi rigid material which rotate about a common axis. One member has indicia for determining its angular relationship with the other. Therefore, aligning one member with one bone from the joint being evaluated and aligning the other member with the other bone of that joint, the angular relationship of the bones can be read from the indicia printed on the first member. By making successive measurement of this type, the range of motion of the joint is determined.

In most cases, goniometers of this design are constructed of clear or translucent plastic, or of sheet metal. Thickness varies between 0.040 inches up to about 0.125 inches for each piece. The sizes vary greatly from small goniometers to measure the joints of the hand to large goniometers to measure the shoulder and elbow. The information printed onto these goniometers is in angular gradations from zero degrees to three hundred sixty, with increments of one, two or five degrees being typical. These goniometers have no function other than rotation of the two halves about their pivot axis from which the angular relationship of these two halves is determined. Examples of such state of the art goniometers include the PC 50 series goniometers manufactured under the Jamar ® name by J. A. Preston Corporation, 60 Page Road, Clifton, N.J. 07012. Another example is the 6 inch plastic goniometer manufactured by North Coast Medical, Inc., 450 Salmar Avenue, Campbell, Calif. 95008.

Another type of goniometer recently introduced is the digital goniometer. This design is virtually the same as those described above, except it includes rotation sensing technology to produce a digital LCD readout of the angle between the two (2) halves. This type typically has a moving zero point, data storage, and a computer interface output in addition to the digital LCD readout. A battery provides electrical power. This type is generally constructed of molded plastic and metal parts and includes a circuit board containing the necessary electronic components for rotation sensing, the LED display and computer interface. An example of this type of goniometer includes Guymon Model 01129 Goniometer manufactured by J. A. Preston Corp.

Because of the importance of range of motion to physiological well-being, it is important that range of motion measurements not only be accurate, but be repeatedly accurate. Accuracy is important to determine in absolute terms the exact degree of motion impairment and to measure the degree of improvement (or the lack thereof) over time or as treatments are administered. The results of range of motion measurements are critical to evaluation of actual loss of function, which in turn is critical to resolution of health insurance and workman's compensation claims. These measurements are also critical to determining the proper and most appropriate treatment.

Using the goniometers currently available such as those described above, it is common for errors in the range of motion measurement to typically be on the order of 2 to 5% from one measurement to the next by the same examiner and on the order of 5 to 10% from one measurement to the next by different examiners. There is therefore a need for a goniometer design that reduces to a minimum both intra-examiner and inter-examiner error. There is also a need for a goniometer which reduces the risk of error in transcription of the angular measurement read, and errors induced by the pain felt by the patient during the measurement process, either from the presence of the goniometer being brought too close to injured tissue or from injured/deformed extremities interfering with the configuration of the goniometer. There is also a need for a goniometer which is easily and accurately aligned with the center line of the bones of the joint being measured. Finally, there is a need for a goniometer which minimizes errors induced by manipulation of the goniometer itself.

SUMMARY OF THE PRESENT INVENTION

The present invention is directed to a system for measuring range of motion and for inputting that range of motion data to a computer. The system is comprised of a goniometer for measuring the range of motion of a joint and for producing a range of motion signal from that measurement. A plurality of switches is carried by the goniometer for producing control signals. An interface receives the range of motion signal and digitizes that signal to produce range of motion data. The interface also receives the control signals for controlling the input of the range of motion data to the computer.

According to one embodiment of the invention, the plurality of switches includes a first push button for producing a first control signal for determining where in the computer the range of motion data is stored, a second push button for producing a second control signal for controlling when the range of motion data is input, and a third push button for producing a third control signal for determining the sign of the range of motion data.

The goniometer includes a reference member, a moveable member, and a pivot pin for pivotally connecting the moveable member to the reference member. According to one embodiment of the present invention, the reference member and the moveable member have opaque edges. The reference member and the moveable member may have clear center portions surrounded by the opaque edges. At least one of the reference member or the moveable member carries a centering line down its center.

According to another embodiment of the invention, the goniometer may be sized for use with the joints of the hand or the wrist. In such an embodiment, the moveable member may carry a notch at the end distal of the pivot point to effectively shorten the moveable member.

The goniometer of the present invention may also be sized for use with the elbow joint. According to that embodiment, one of the reference member or moveable member carries indicia and the other member carries a pointer in such a manner that the degree to which the moveable member is pivoted with respect to the reference member is indicated by the position of the pointer relative to the indicia.

The present invention is also directed to a method for measuring range of motion data and inputting said range of motion data to a computer which is comprised of the following steps.

A goniometer is positioned relative to a joint. Thereafter, the joint is manipulated, passively or actively, to determine the range of motion. A computer's display is viewed to insure that the range of motion information being produced will be stored in the location within the computer's memory assigned to receive information about that joint. If not, a push button is depressed to move the cursor on the display until the appropriate location for that data is obtained. Thereafter, a second push button is depressed to input the data. If it is determined that the sign of the data (+ or −) must be changed, a third push button is depressed prior to the input of the data.

The apparatus and method of the present invention provide for the measurement of range of motion and the input of that range of motion data into a computer in a fast and reliable manner. By transferring control over data input to the goniometer, reliability and repeatability are increased. Additionally, the construction of the goniometer permits accurate placement of the goniometer and helps eliminate accidental contact between the doctor or technician and injured patients. Those and other advantages and benefits of the present invention will become apparent from the Detailed Description of The Preferred Embodiment hereinbelow.

BRIEF DESCRIPTION OF THE DRAWINGS

For the present invention to be clearly understood and readily practiced, a preferred embodiment will now be described, by way of example only, with reference to the accompanying figures wherein.

DETAILED DESCRIPTION OF THE PREFERRED EMBODIMENT

Figure 1:
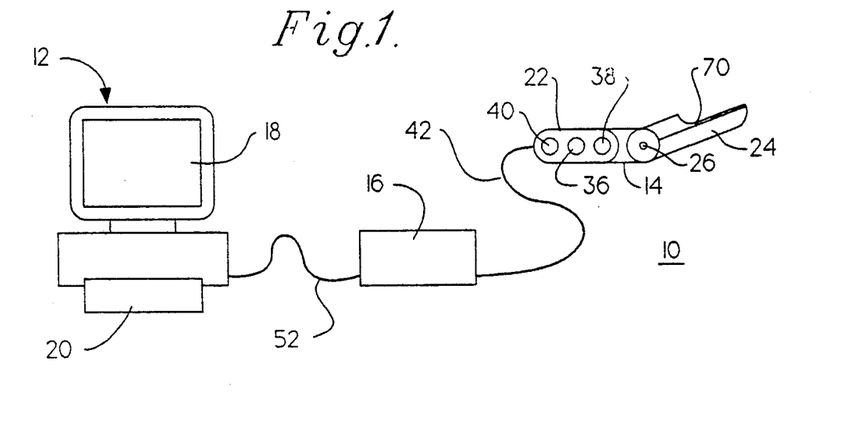
FIG. 1 is a diagram illustrating the system of the present invention which produces range of motion data and inputs that data to a computer.

The present invention is directed to a system 10, illustrated in FIG. 1, for measuring and inputting range of motion (ROM) data to a computer 12. The system 10 is comprised of a goniometer 14 and an interface/power supply device 16. The data produced by the system 10 is input to the computer 12 which may include a CRT 18 and a keyboard 20. The computer 12 may be any type of known, commercially available computer which is capable of being programmed to receive data, for example, from a mouse.

Figure 2:
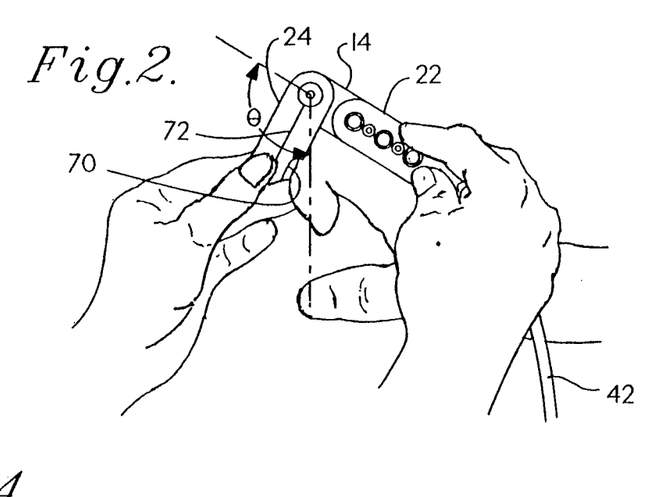
FIG. 2 illustrates that portion of the system which is comprised of a goniometer sized for use in conjunction with the hand or wrist.
Figure 4:
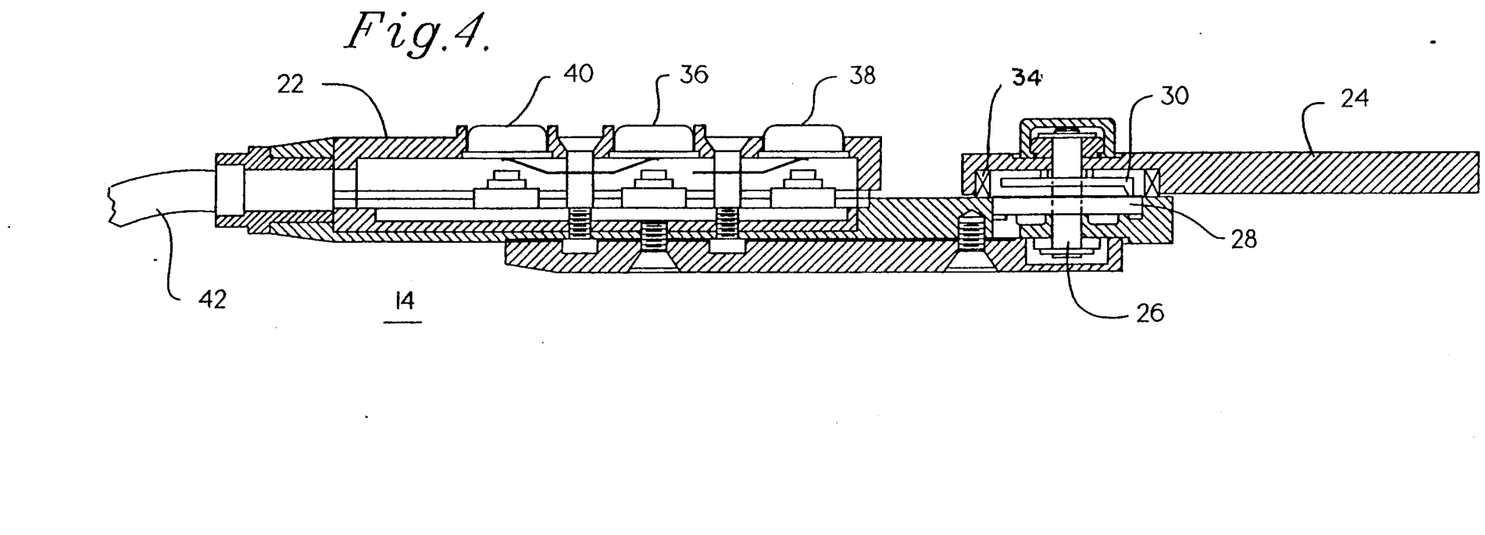
FIG. 4 is a cross-sectional view of the goniometer illustrated in FIG. 2.
Figure 7:
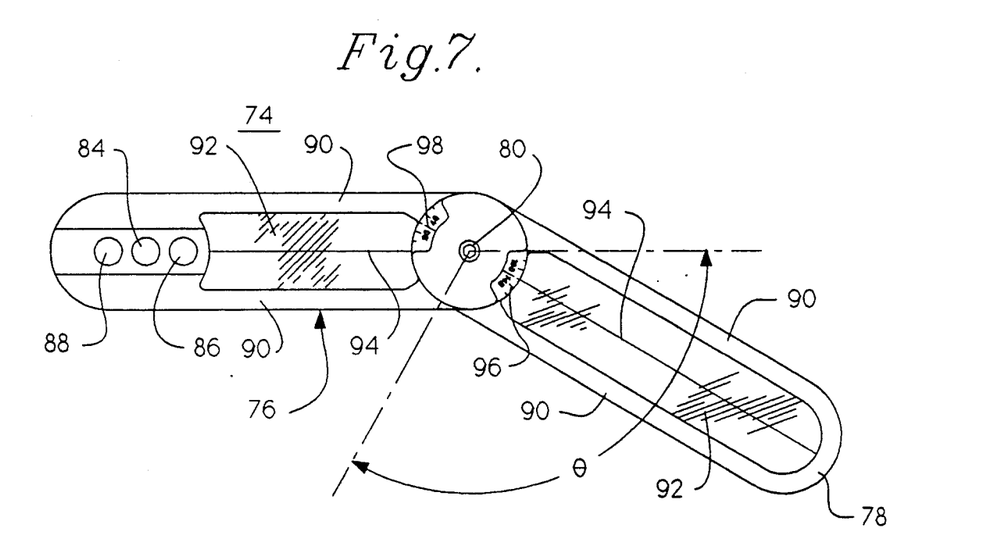
FIG. 7 illustrates another type of goniometer, sized for use with the elbow joint.
Figure 8:
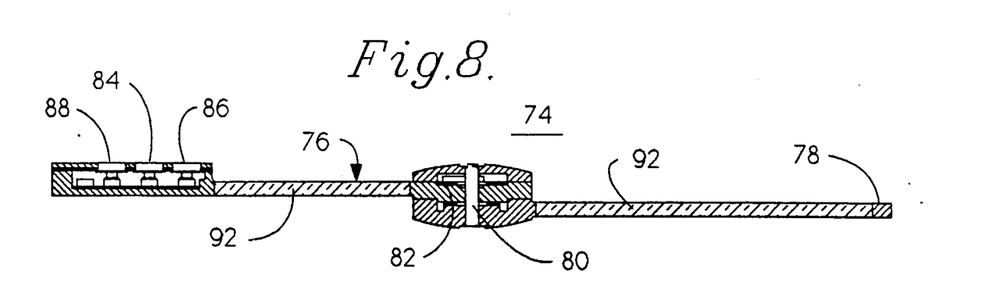
FIG. 8 is a cross-sectional view of the goniometer illustrated in FIG. 7.

The goniometer 14 may be sized for use with the joints of the hand or wrist as shown in FIGS. 1, 2, and 4, may be sized for use with the elbow joint as shown in FIGS. 7 and 8, or it may be sized for use with other joints of the body (not shown).

Referring to the goniometer shown in FIGS. 1 and 2, and in cross-section in FIG. 4, the goniometer is comprised of a reference member 22 and a moveable member 24. A pin 26 connects the moveable member 24 to the reference member 22 in such a manner as to enable the moveable member 24 to pivot about pin 26 with respect to the reference member 22. In that manner, pin 26 forms a pivot axis. A bearing 34, seen in FIG. 4, may be provided to enable the moveable member 24 to pivot smoothly with respect to the reference member 22.

Figure 5:
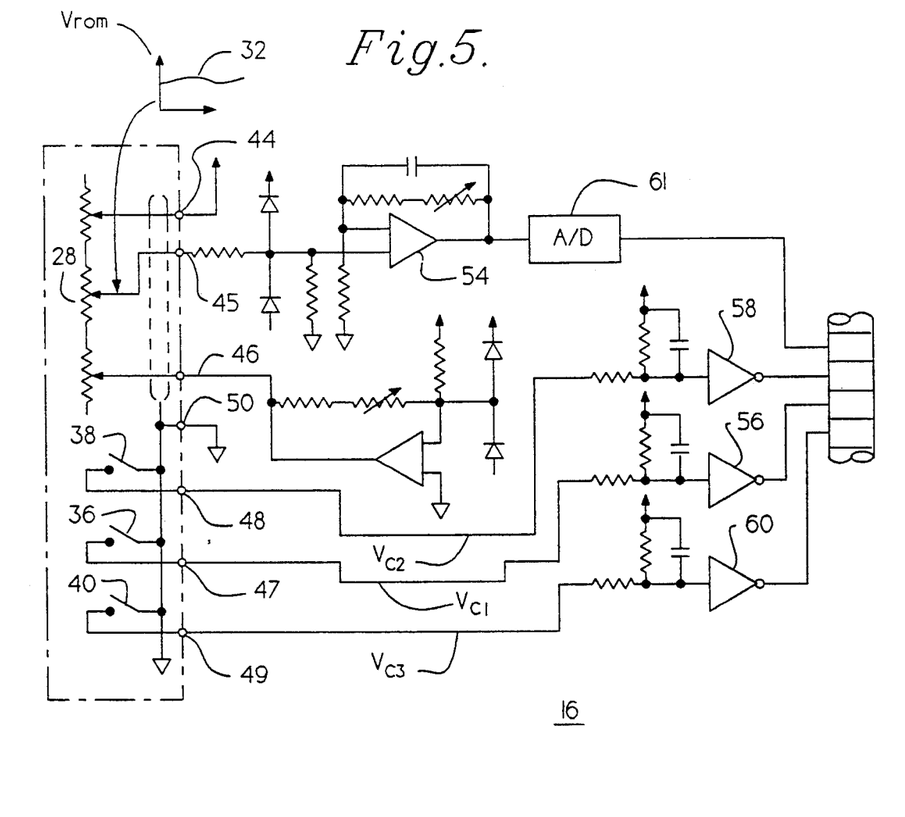
FIG. 5 is an electrical schematic of the system of the present invention.

A rotary potentiometer is comprised of a resistive element 28 carried by the reference member 22 and a wiper 30 carried by the moveable member 24. In that manner, movement of the moveable member 24 with respect to the reference member 22 causes the position of the wiper 30 with respect to the resistive element 28 to vary. Thus, an analog range of motion signal $V_{rom}$ 32, seen in FIG. 5, is produced by the goniometer 14. In the disclosed embodiment, $V_{rom}$ 32 is an analog voltage having a magnitude dependent upon the angular relationship between the moveable member 24 and the reference member 22.

The moveable member 24 of the goniometer 14 may be provided with a notch 70 which effectively shortens the length of the member 24. The value of such a notch 70 can be seen in FIG. 2. In the event that the distal interphalangeal joint is swollen, the notch 70 will still permit an accurate reading to be taken while at the same time providing a longer member 24 thereby enabling the technician or doctor to more easily operate the goniometer 14.

As seen in FIG. 2, the goniometer 14 may be constructed to enable the moveable member 24 to pivot to an angle theta of plus or minus 135° with respect to the centerline of member 22, for a total movement of 270°. Other constructions are possible which permit full 360° rotation. The members 22 and 24 may be constructed of metal such that the edges are opaque thereby enabling the technician or physician to accurately assess the position of the instrument with respect to the patient. That enables more accurate readings and prevents inadvertent contact with sensitive or injured tissue. Finally, the moveable member 24 may carry a centering line 72 down the center thereof. The purpose of the centering line 72 is to enable accurate placement of the goniometer 14, particularly when wrist examinations are being performed.

The goniometer 14 carries three push buttons. A first push button 36 for producing a first control signal $V_{c1}$, seen in FIG. 5, a second push button 38 for producing a second control signal $V_{c2}$, and a third push button 40 for producing a third control signal $V_{c3}$. The control signals $V_{c1}$, $V_{c2}$, and $V_{c3}$, are used for controlling the input of the range of motion data generated by the goniometer 14 to the computer 12. The use of the push buttons 36, 38, and 40 will be discussed in greater detail hereinbelow in conjunction with FIG. 3.

The goniometer 14 is connected to the interface/-power supply device 16 through a cable 42. As seen in FIG. 5, the cable 42 is a seven conductor cable with three conductors 44, 45, and 46, being used in conjunction with the potentiometer, three conductors 47, 48, and 49, being used with the three push buttons 36, 38, and 40, respectively, and one conductor 50 being used as a shielded ground.

The $V_{rom}$ signal 32 available on conductor 45 is conditioned by an operational amplifier 54 and associated circuitry as shown if FIG. 5. In a similar manner, control signals $V_{c1}$, $V_{c2}$, and $V_{c3}$ are conditioned by operational amplifiers 56, 58, and 60, respectively, and their associated components. The control signals are then input from device 16 to the computer 12 through a cable 52.

The $V_{rom}$ signal 32 is input to an analog to digital converter 61 within device 16. Alternatively, the conversion may be performed by a converter card in the computer 12. The analog to digital converter 61 is a conventional twelve bit converter which converts the signal $V_{rom}$ 32 into digital values. In that manner, the $V_{rom}$ signal 32 is converted into digital range of motion data which may be input to computer 12 through the cable 52 in accordance with control signals $V_{c1}$, $V_{c2}$, and $V_{c3}$.

Figure 3:
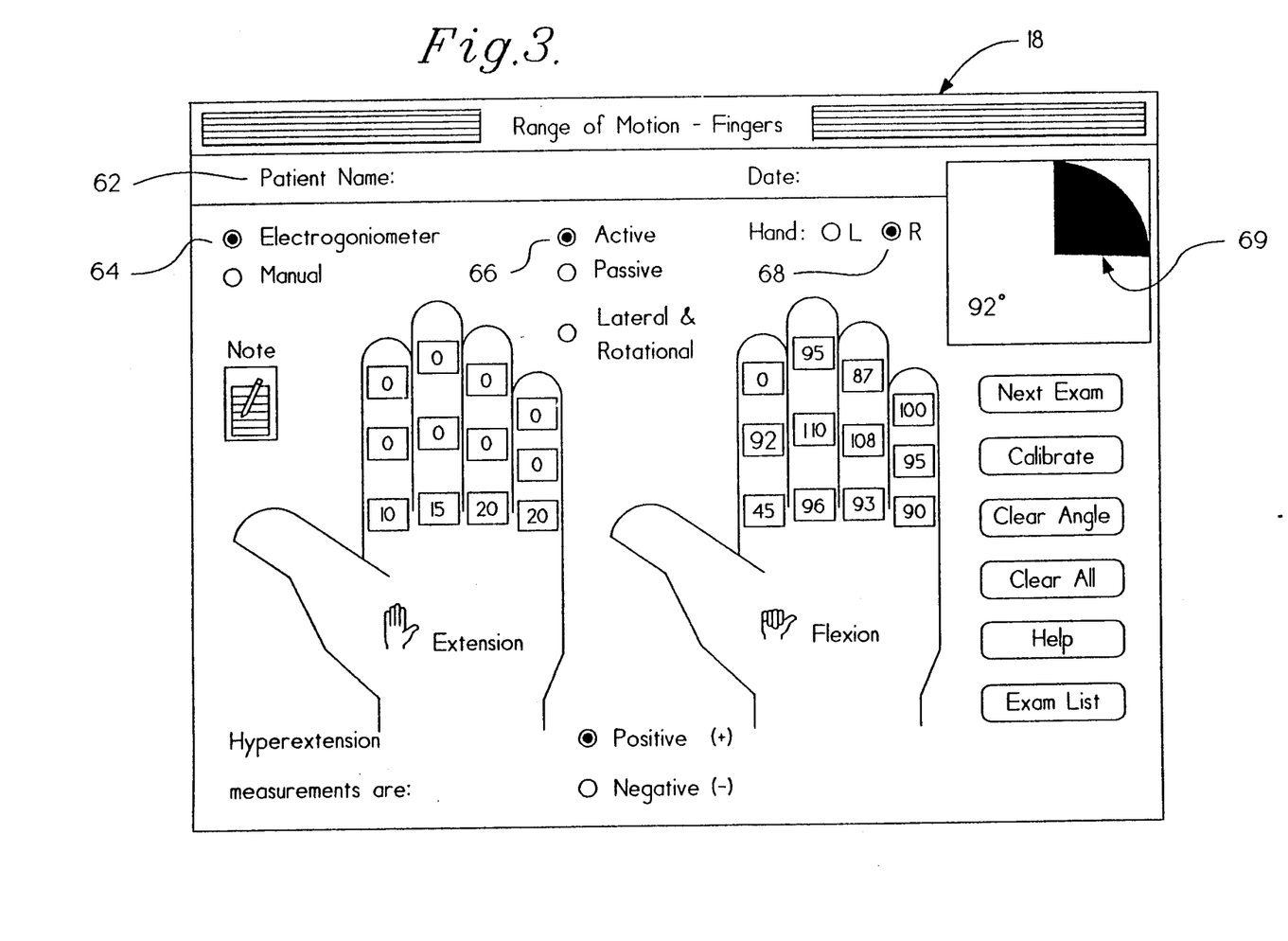
FIGS. 3 and 6 illustrate CRT displays which may be used in conjunction with the system of the present invention.

Turning now to FIGS. 2 and 3, the goniometer 14 is seen in FIG. 2 positioned to measure the range of motion of the proximal interphalangeal joint of the index finger of the right hand. The computer 18 may be programmed to display the information illustrated in FIG. 3 in conjunction with taking range of motion measurements with respect to the fingers. A program for producing a screen as illustrated in FIG. 3 is commercially available from the Greenleaf Medical Corporation under the name EVAL. It should be understood, however, that the system 10 of the present invention need not be operated in conjunction with the aforementioned program. Any suitable computer program which requires as input range of motion data can be used in conjunction with the system 10.

As seen in FIG. 3, various information appears on the screen relating to the identity of the patient 62, the type of instrument being used 64, the type of test being performed 66, the hand being tested 68, and the instantaneous value 69 of $V_{rom}$. Each of the joints of the right and left hand are represented by a box having a value therein. If the joint has been tested, a ROM value appears in the box. If a joint has not been tested, the value 0 appears in the box.

The cursor appears at the box for the proximal interphalangeal joint of the right index finger, which corresponds to the placement of the goniometer 14. If the cursor were not positioned at the appropriate box, depression of push button 36 would cause the cursor to move to another location according to its programming. Thus, continual depression of push button 36 enables the cursor to be positioned on the box representing the joint which is being measured. In that manner, the first control signal $V_{c1}$ enables the user to access the location in the computer's memory which has been assigned to store the information relative to the joint being tested.

After the cursor has been positioned in the proper location, the second push button 38 is depressed. The digital value representing the magnitude of the $V_{rom}$ signal 32 at the time the second push button 38 is depressed is the value which appears in the box where the cursor is located. If it should be determined that the sign of that value needs to be changed, depression of the third push button 40 prior to depression of push button 38 causes the sign of the stored value to be changed. In that manner, control of the input of the data produced by the goniometer 14 is located at the goniometer 14 thereby eliminating or reducing errors and inconsistencies.

Figure 6:
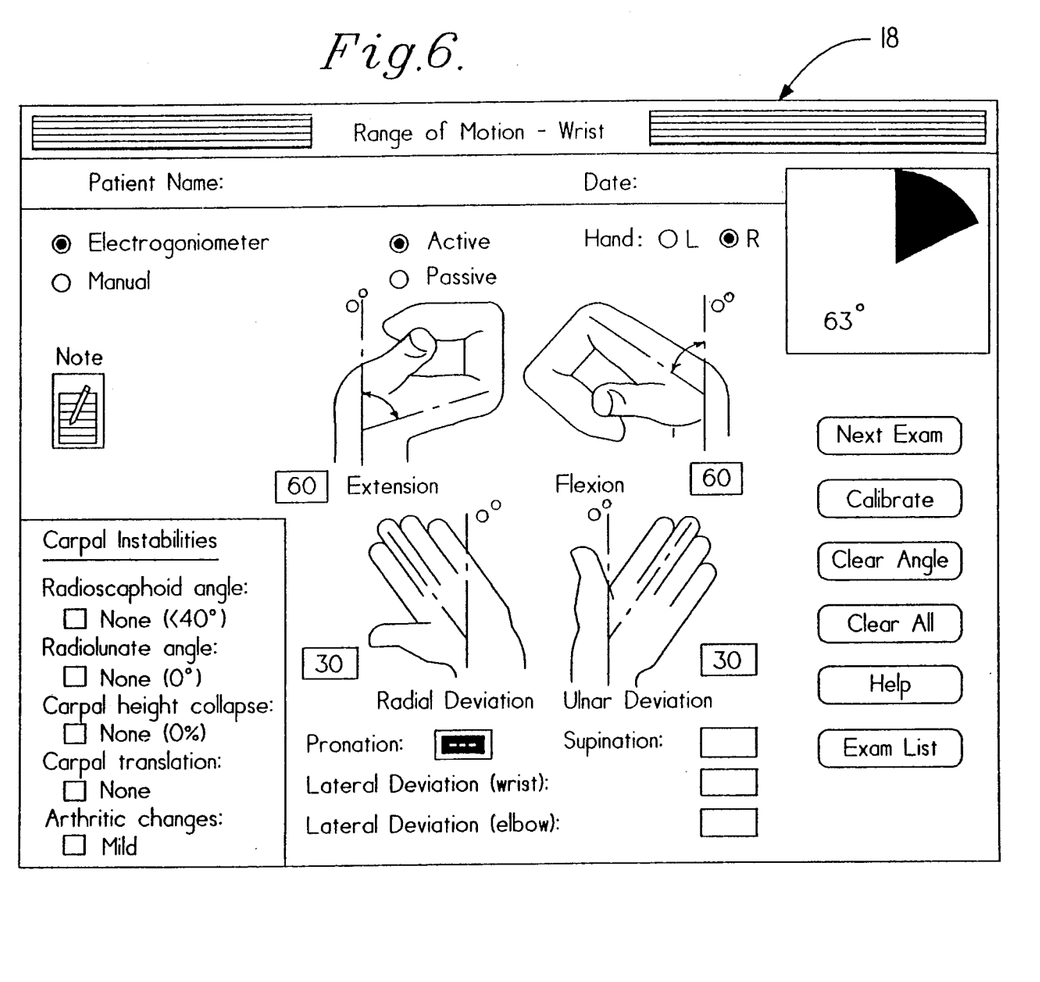

The goniometer 14 may also be used in conjunction with known types of wrist examinations. An appropriate CRT display for wrist examinations is illustrated in FIG. 6. However, as previously noted, the particular software being run on computer 12 is not a feature of the present invention. The system 10 of the present invention may be used in conjunction with any software run on a computer capable of receiving input commands through an external device, such as a mouse.

The goniometer 14 seen in FIGS. 1, 2, and 4, is sized to be used in conjunction with the joints of the hand or the wrist. However, the system 10 may function equally well with other sized goniometers. For example, illustrated in FIGS. 7 and 8 is a goniometer 74 sized for use with the elbow joint. The goniometer 74 is constructed in a manner similar to the goniometer 14. The goniometer 74 has a reference member 76 pivotally connected to a moveable member 78 through a pivot pin 80. The moveable member 78 is capable of moving through an angle theta of plus or minus 170° with respect to the centerline of the reference member 76. A potentiometer 82 is positioned as previously disclosed so that an analog signal representative of the angle between the moveable member 78 and the reference member 76 is produced. The goniometer 74 also carries a first push button 84, a second push button 86, and a third push button 88 which perform the same functions as discussed above in conjunction with push buttons 36, 38, and 40, respectively.

The goniometer 74 differs from the goniometer 14 in two significant respects. First, although the edges 90 of the reference member 76 and moveable member 78 are opaque, the center portions 92 are transparent. The transparent center portions 92 each carry a centering line 94 to enable the goniometer 74 to be accurately positioned. Second, the reference member 76 carries indicia 96 while the moveable member 78 carries a pointer 98. The pointer 98 cooperates with indicia 96 in such a manner that the angular displacement of the moveable member 78 relative to the center line of reference member 76 can be discerned from the position of the pointer 98 relative to the indicia 96.

The present invention is also directed to a method for measuring range of motion data, and inputting that range of motion data to a computer, which is comprised of the following steps. A goniometer 14 is positioned relative to a joint. Thereafter, the joint is manipulated, passively or actively, to determine the range of motion. A computer's display is viewed to insure that the range of motion information being produced will be stored in the location within the computer's memory assigned to receive information about that joint. If not, push button 36 is depressed to move the cursor on the display until the appropriate location for that data is obtained. Thereafter, the second push button 38 is depressed to input the data. If it is determined that the sign of the data (+ or −) must be changed, the third push button 40 is depressed prior to depressing push button 38.

The apparatus and method of the present invention provide for the measurement of range of motion and the input of that range of motion data into a computer in a fast and reliable manner. By transferring control over data input to the goniometer, reliability and repeatability are increased. Additionally, the construction of the goniometer permits accurate placement of the goniometer and helps eliminate accidental contact between the doctor or technician and injured patients. While the present invention has been described in connection with an exemplary embodiment thereof, it will be understood that many modifications and variations will be readily apparent to those of ordinary skill in the art. This disclosure and the following claims are intended to cover all such modifications and variations.

What is claimed is:

1. A system for measuring and inputting range of motion data to a computer, comprising:
    goniometer means having a movable member pivotally connected to a reference member for producing an analog range of motion signal representative of the position of said movable member relative to said reference member, each of said movable member and reference member having clear center portions surrounded by opaque edges;
    a plurality of switch means carried by said goniometer means for producing a plurality of control signals;
    interface means including an analog to digital converter means for receiving said range of motion signal and for converting said signal to digital range of motion data, said interface means also for receiving said plurality of control signals for controlling the input of said digital range of motion data to the computer remote from said goniometer means.

2. The system of claim 1 wherein said plurality of switch means includes a first push button for producing a first control signal for determining where in the computer said range of motion data is stored, a second push button for producing a second control signal for controlling when said range of motion data is input, and a third push button for producing a third control signal for determining the sign of said range of motion data.

3. The system of claim 1 wherein at least one of said reference member and said movable member carries a centering line down the center of said member.

4. The system of claim 1 wherein said reference member and said movable member are sized for use with the joints of the hand.

5. The system of claim 4 wherein said movable member carries a notch at the end distal of said pivot means.

6. The system of claim 1 wherein one of said reference member and said movable member carries indicia and said other member carries a pointer in such a manner that the degree to which said movable member is pivoted with respect to said reference member is indicated by the position of said pointer relative to said indicia.

7. The system of claim 1 wherein said reference member and said movable member are sized for use with the elbow joint.

8. A system for measuring and inputting range of motion data to a computer having a screen for displaying the position of a cursor representative of the location in the computer's memory where range of motion data may be stored, said system comprising:
    goniometer means having a movable member pivotally connected to a reference member for producing an analog range of motion signal representative of the position of said movable member relative to said reference member;
    a plurality of switch means carried by said goniometer means for producing first and second control signals;
    interface means including an analog to digital converter for receiving said range of motion signal and for converting said signal to digital range of motion data, said interface means also receiving said first control signal and inputting said first control signal to the computer for controlling the position of the cursor, said interface means also receiving said second control signal and inputting said second control signal to the computer to control the input of said range of motion data to the computer.

* * * * *

UNITED STATES PATENT AND TRADEMARK OFFICE
CERTIFICATE OF CORRECTION

PATENT NO. : 5,163,228
DATED : November 17, 1992
INVENTOR(S) : Glenn R. Edwards

It is certified that error appears in the above-identified patent and that said Letters Patent is hereby corrected as shown below:

Col. 2, line 14, delete "LED" and substitute therefor --LCD--.

Col. 5, line 29, delete "if" and substitute therefor --in--.

Col. 5, line 48, delete "18" and substitute therefor --12--.

Signed and Sealed this

Thirtieth Day of November, 1993

Attest:

BRUCE LEHMAN

Attesting Officer

Commissioner of Patents and Trademarks